United States Patent
Hsiao et al.

(10) Patent No.: US 9,150,615 B2
(45) Date of Patent: Oct. 6, 2015

(54) PROCESS FOR THE PREPARATION OF LEUPROLIDE AND ITS PHARMACEUTICALLY ACCEPTABLE SALTS

(71) Applicant: ScinoPharm Taiwan, Ltd., Shan-Hua, Tainan (TW)

(72) Inventors: Tsung Yu Hsiao, Tainan (TW); Shih Wei Lee, Tainan (TW)

(73) Assignee: ScinoPharm Taiwan, Ltd., Shan-Hua (TW)

( * ) Notice: Subject to any disclaimer, the term of this patent is extended or adjusted under 35 U.S.C. 154(b) by 0 days.

(21) Appl. No.: 14/132,169

(22) Filed: Dec. 18, 2013

(65) Prior Publication Data

US 2015/0166602 A1    Jun. 18, 2015

(51) Int. Cl.
*C07K 7/06* (2006.01)

(52) U.S. Cl.
CPC ........................................ *C07K 7/06* (2013.01)

(58) Field of Classification Search
None
See application file for complete search history.

(56) References Cited

U.S. PATENT DOCUMENTS

2005/0004000 A1 *    1/2005   Shechter et al. .................. 514/2

FOREIGN PATENT DOCUMENTS

| CN | 100529757 C | 8/2009 | |
|---|---|---|---|
| CN | 101538315 A | 9/2009 | |
| CN | 1865280 B | 3/2012 | |
| CN | 101597325 B | 4/2012 | |
| CN | 102464702 A | 5/2012 | |
| EP | 2119725 A1 | 11/2009 | |
| WO | WO 2008/044890 | * 4/2008 | ............... C07K 7/06 |
| WO | 2011/148384 A1 | 12/2011 | |

* cited by examiner

*Primary Examiner* — Maury Audet
(74) *Attorney, Agent, or Firm* — Enshan Hong; VLP Law Group LLP

(57) ABSTRACT

The invention provides a process for the preparation of leuprolide or its pharmaceutical acceptable salts by a combination of solid phase synthesis and post assembly solution phase amidation. The invention also relates to applying a non-protected leuprolide precursor to prepare leuprolide or its pharmaceutically acceptable salts.

12 Claims, 2 Drawing Sheets

PROCESS FOR THE PREPARATION OF LEUPROLIDE AND ITS PHARMACEUTICALLY ACCEPTABLE SALTS

BACKGROUND OF THE INVENTION

1. Field of the Invention

The present application relates to a process for preparation of leuprolide and its pharmaceutically acceptable salts.

2. Description of the Related Art

Leuprorelin or leuprolide acetate belongs to a family of drugs called gonadotropin-releasing hormone (GnRH) analogues. It is a synthetic nonapeptide analog which acts as an agonist at pituitary GnRH receptors. The chemical name is 5-oxo-L-prolyl-L-histidyl-L-tryptophyl-L-seryl-L-tyrosyl-D-leucyl-L-leucyl-L-arginyl-N-ethyl-L-prolinamide acetate (salt) and its primary sequence is Pyr-His-Trp-Ser-Tyr-D-Leu-Leu-Arg-Pro-NHEt. It may be utilized in the treatment of hormone-responsive cancer such as prostate or breast cancer, estrogen-dependent conditions, such as endometriosis or utrine fibroids, and to control precocious puberty. Leuprolide acetate is marketed as Viadur by Bayer AG, as Eligard by Sanofi-Aventis and as Lupron by Takeda Abbott Pharmaceuticals (TAP) in the United States.

Recently some syntheses utilized for preparing leuprolide or leuprolide acetate were disclosed in EP 2,119,725A1, WO 2008/44890A1 and WO 2011/148384A1.

European Patent Application EP 2,119,725A1 describes a method of preparing a peptide which is a C-terminal amide derivative, which comprises providing an amino acid attached in its C-terminal to a super-acid labile resin; coupling said amino acid with another amino acid in the presence of a coupling reagent; repeating the coupling step to obtain a peptide, wherein the peptide is protected with at least one protecting group which remains on the peptide upon its cleavage from the resin; cleaving said protected peptide from the resin by admixing with a mild acidic solution; and amidating the obtained protected peptide with a suitable amine.

FIG. 1 illustrates the route to leuprolide disclosed in EP 2,119,725A1. The preparation of leuprolide precursor [Pyr-His(Trt)-Trp-Ser(tBu)-Tyr(tBu)-D-Leu-Leu-Arg(Pbf)-Pro-OH] is cleaved from the resin by admixing a 1% TFA in DCM. Although the applicant emphasizes the process is performed under mild condition, the protecting groups of the leuprolide precursor and the super-acid labile resin cannot be removed to obtain the leuprolide precursor simultaneously. Thus, such a process inevitably needs to increase additional operations. Disadvantages of the process include resulting in a more tedious process of preparing leuprolide and other costly work-up procedures required at additional steps. Besides, since it is difficult to cleave the leuprolide precursor from a general acid-labile resin with a mild acidic solution, the process for preparing leuprolide is limited to the use of a super-acid labile resin. Furthermore, it is noted that the leuprolide precursor is prepared by coupling a crude peptide cleaved from the super acid-labile resin, and the coupling reaction involves the addition of TBTU/HOBT in the activation of carboxyl group of the peptide. However, HOBT is explosive and not suitable for performing the preparation. Therefore, the method does not have the excellent applicability in terms of the preparation of leuprolide.

Another route, disclosed in WO 20111148384A1 and shown in FIG. 2, which relates to a process for the preparation of leuprolide or its pharmaceutical acceptable salts thereof by synthesizing the peptide fragments by solid phase [7 and 5 amino acids fragment, i.e., Pyr-His(Trt)-Trp(Boc)-Ser(tBu)-D-Leu-Leu-OH and Pyr-His(Trt)-Trp(Boc)-Ser(tBu)-Tyr(tBu)-OH] and solution phase [2 and 4 amino acids fragment, i.e., H-Arg(Pbf)-Pro-NHEt and H-D-Leu-Leu-Arg(Pbf)-Pro-NHEt] respectively. The final solution phase condensation of these peptide fragments (7+2 and 5+4) led to a nonapeptide leuprolide in the protected form, i.e., Pyr-His(Trt)-Trp(Boc)-Ser(tBu)-D-Leu-Leu-Arg(Pbf)-Pro-NHEt. The protected nonapeptide leuprolide is deprotected to obtained leuprolide, and then leuprolide can be converted into pharmaceutically acceptable salts. Disadvantages of this processes include the synthesis of the materials H-Arg(Pbf)-Pro-NHEt and H-D-Leu-Leu-Arg(Pbf)-Pro-NHEt involves the use of the expensive material, i.e., Pro-NH—CH2CH3. Besides, the cleavage of the 7 and 5 amino acids fragment from the super acid-labile resin is carried out by using 1% TFA in DCM, which is similar to the method disclosed in EP 2,119,725A1. Therefore, there is the same deficiency that the protecting groups of the 7 and 5 amino acids fragment and the super-acid labile resin cannot be simultaneously removed to obtain a leuprolide precursor. Such a process inevitably needs to increase additional operations. Disadvantages of the process include resulting in a more tedious process of preparing leuprolide and other costly work-up procedures required at additional steps. As above, the process for preparing leuprolide is limited to the use of a super-acid labile resin but not suitable for using a general acid-labile resin. Furthermore, it is noted that the protected nonapeptide leuprolide is prepared by coupling the 7 and 5 amino acids fragment cleaved from the super acid-labile resin with the 2 and 4 amino acid fragments, and the coupling reaction involves the addition of HBTU/6-CI-HOBT/DIEA in the activation of carboxyl group of the peptide. However, actually HOBT is explosive and not suitable for performing the coupling reaction. Therefore, the method does not have the excellent applicability in terms of the preparation of leuprolide.

Yet another route, disclosed in WO 2008/44890A1 and shown in FIG. 3, which includes using a super acid-labile resin in the SPPS to prepare a leuprolide derivative, i.e., Pyr-His-Try-Ser(Bzl)-Tyr(Bzl)-D-Leu-Leu-Arg(NO2) which is obtained by adding weak acidic cleavage solution such as 2%-50% TFA/DCM, then the leuprolide precursor is reacted with Pro-NH—CH2CH3 to obtain Pyr-His-Try-Ser(Bzl)-Tyr(Bzl)-D-Leu-Leu-Arg(NO2)-Pro-NH—CH2CH3, and then the side-chain protecting groups are removed through catalytic hydrogen transfer reaction using by Pd/C and cyclohexadiene etc. Disadvantages of this process include the material Pro-NH—CH2CH3 is expensive and the hydrogenation reaction utilized for removing the side-chain protecting groups is also unsafe.

As such, there is a strong demand for a convenient process that is suitable for preparation of leuprolide or its pharmaceutically acceptable salts on a commercial scale with high purity and without complicated and costly purification steps. The present invention addresses this and other needs.

SUMMARY OF THE INVENTION

The present invention relates to a method for preparing leuprolide and its pharmaceutically acceptable salts by the combination of solid and solution phase peptide synthesis.

The method comprises: providing an amino acid derivative attached in its C-terminal to an acid-labile resin, wherein all side chains of said amino acid derivative are protected; cleaving all protecting groups of said amino acid derivative and said resin by reacting with an suitable acidic solution to obtain an deprotected leuprolide precursor; amidating the deprotected leuprolide precursor with a suitable amine in the presence of a coupling reagent to obtain leuprolide, and then optionally converting leuprolide into its pharmaceutically acceptable salts.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

DETAILED DESCRIPTION OF THE PRESENTLY PREFERRED EMBODIMENTS

Figure 1:
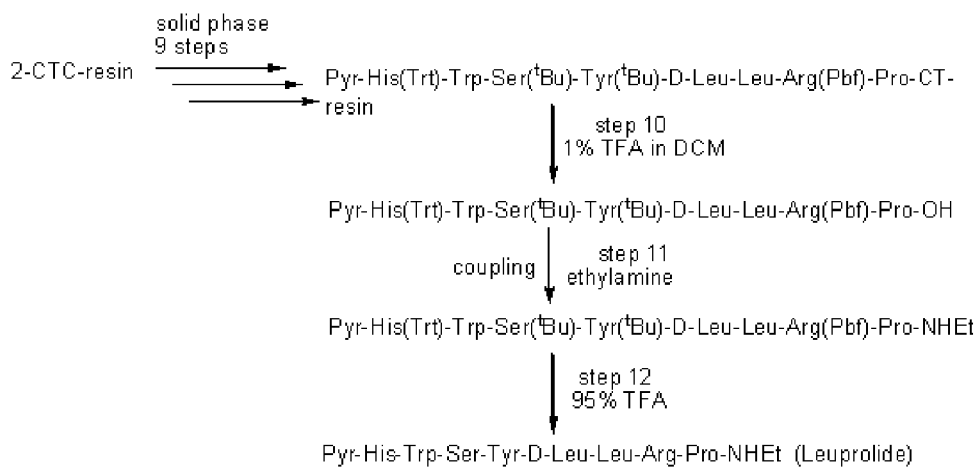
FIG. 1 shows a route to leuprolide disclosed in EP 2,119,725A1.
Figure 2:
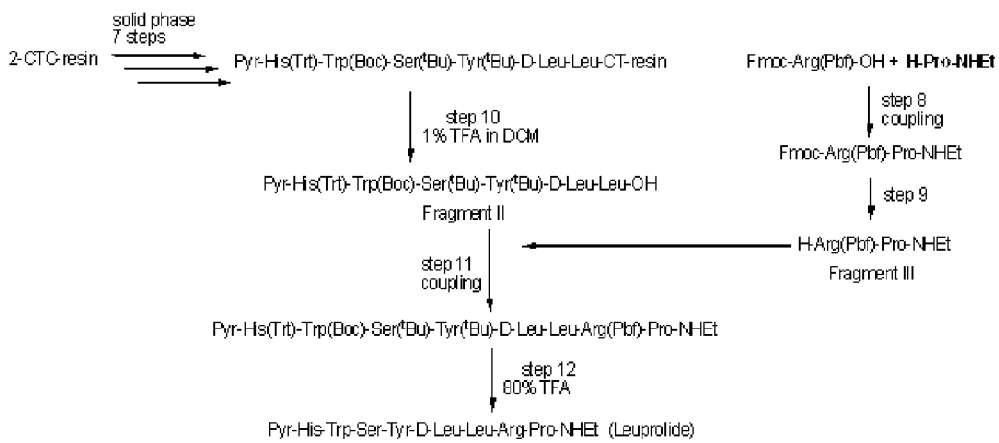
FIG. 2 shows a route to leuprolide disclosed in PCT patent application No. 2011/148384.
Figure 3:
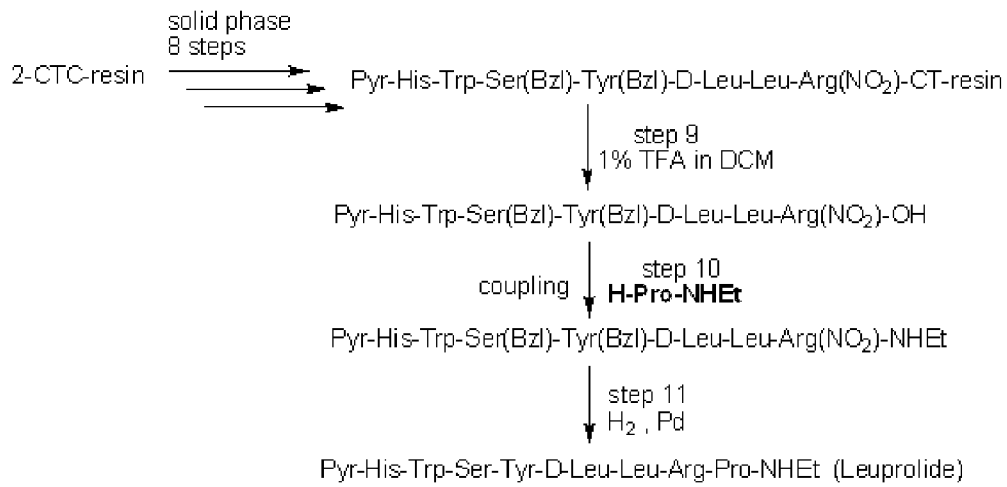
FIG. 3 shows a route to leuprolide disclosed in PCT patent application No. 2008/044890.
Figure 4:
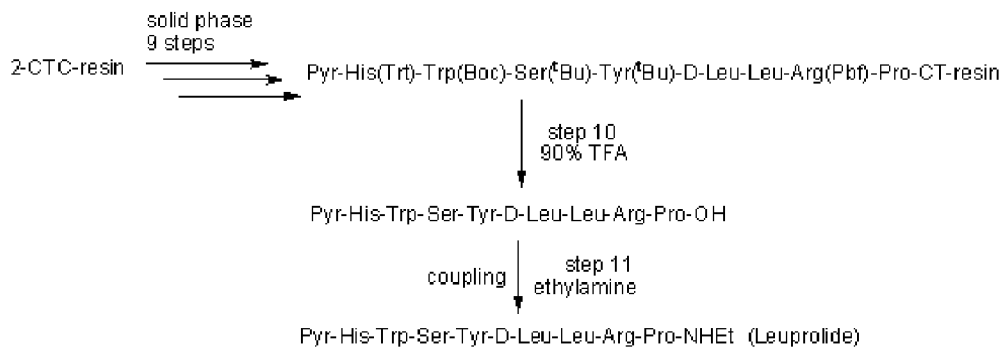
FIG. 4 shows a route to leuprolide as disclosed by the present application.

The present invention provides a novel, efficient, safe and easily operating method for preparing leuprolide and its pharmaceutical acceptable salts by the combination of solid and solution phase synthesis. The method comprises providing an amino acid derivative attached in its C-terminal to an acid-labile resin, wherein all side chains of said amino acid derivative are protected; then cleaving all protecting groups of said amino acid derivative and said resin by reacting with an suitable acidic solution to obtain an deprotected leuprolide precursor; and then amidating the deprotected leuprolide precursor with a suitable amine in the presence of a coupling reagent. Subsequently, the crude product was purified by reverse phase HPLC to obtain fractions containing desired leuprolide salt at a purity of more than 99% (UPLC).

According to the present invention, the amino acid derivative attached in its C-terminal to an acid-labile resin is prepared by providing an protected amino acid, attached in its C-terminal to an acid-labile resin; coupling the first protected amino acid with a second protected amino acid in the presence of a coupling reagent to obtain an amino acid fragment, and then coupling obtained fragment with another protected amino acid in the same way, step-by-step, to provide the amino acid derivative attached in its C-terminal to an acid-labile resin.

Advantageously, the present invention provides a concise synthetic route to prepare leuprolide and its pharmaceutical acceptable salts. In some embodiments, several acid labile resins can be utilized in the present invention; in contrast with other prior art methods that can only employ a specific resin, in particular super acid-labile resin. In addition, the present invention reduces the steps of synthesizing leuprolide. Surprisingly, it is noted that the amidation of the deprotected leuprolide precursor in the presence of a suitable coupling reagent and a specific molar equivalent of ethylamine can provide a high yield and high purity of the final product. Accordingly, the present invention avoids a tedious process as disclosed in the prior art and is more suitable for a large-scale production of leuprolide and its pharmaceutically acceptable salts.

As utilized herein, the term "coupling reagent" refers to the reagent utilized for the activation of the carboxy group of the protected or deprotected peptide fragment.

As utilized herein, the term "suitable acidic solution" refers to a solution comprising an acid in an inert organic solvent, in a concentration such that the protecting groups are enough to be removed during the cleavage of the peptide from the resin.

As utilized herein, the term "protecting group" refers to a moiety that is formed to render a functional moiety unreactive. The protecting group can be removed so as to restore the functional moiety to its original state. Various protecting groups and protecting reagents, including hydroxy protecting groups, are well known to one of ordinary skill in the art and include compounds that are disclosed in Protective Groups in Organic Synthesis, 4th edition, T. W. Greene and P. G. M. Wuts, John Wiley & Sons, New York, 2006, which is incorporated herein by reference in its entirety.

One embodiment of the present invention relates to a process for the preparation of leuprolide or its pharmaceutically acceptable salts by providing an amino acid derivative attached in its C-terminal to an acid-labile resin, wherein all side chains of said amino acid derivative are protected; cleaving all protecting groups of said amino acid derivative and said resin by reacting with an suitable acidic solution to obtain an deprotected leuprolide precursor; amidating the deprotected leuprolide precursor with a specific equivalent of ethyl amine in the presence of a suitable coupling reagent to obtain leuprolide, and then optionally converting leuprolide into its pharmaceutically acceptable salts.

In accordance with the invention, the coupling reagent utilized in the amidation step is selected from the group consisting of N,N'-Diisopropylcarbodiimide (DIC), 1-Ethyl-3-(3-dimethylaminopropyl)carbodiimide (EDCI) and benzotriazol-1-yl-oxytripyrrolidinophosphonium hexafluorophosphate (PyBOP).

Optionally, the acid-labile resin comprises general acid-labile resin, such as para-hydroxybenzyl alcohol (PHB) resin (e.g. Wang resin) and 4-hydroxymethylphenoxyacetyl (HMPA) resin (e.g. HMPA-NovaGel™), etc. and super-acid labile resin, such as 2-chlorotrityl chloride (2-CTC) resin, 4-(2',4'-dimethoxyphenyl-hydroxymethyl)-phenoxy resin (Rink acid resin) and 4-hydroxymethyl-3-methoxyphenoxy-butyric acid (HMPB) resin (e.g. HMPB-MBNA resin), etc.

Preferably, the suitable acidic solution utilized for obtaining is a solution comprising at least 80 volume % of trifluoroacetic acid (TFA).

Before the amidation step, preferably the deprotected leuprolide precursor is isolated. Optionally, the isolation is by precipitation, crystallization, extraction, or chromatography. Preferably, the isolation is by precipitation.

According to the present invention, the deprotected leuprolide precursor cleaved from the resin is an amino acid derivative having the sequence of: Pyr-His-Trp-Ser-Tyr-D-Leu-Leu-Arg-Pro-OH. The amidation step comprises reacting the deprotected leuprolide precursor with ethyl amine in water in the presence of a coupling reagent to obtain leuprolide having the sequence of: Pyr-His-Trp-Ser-Tyr-D-Leu-Leu-Arg-Pro-NHEt (See Scheme 1), and then optionally converting leuprolide into its pharmaceutically acceptable salts.

Scheme 1:
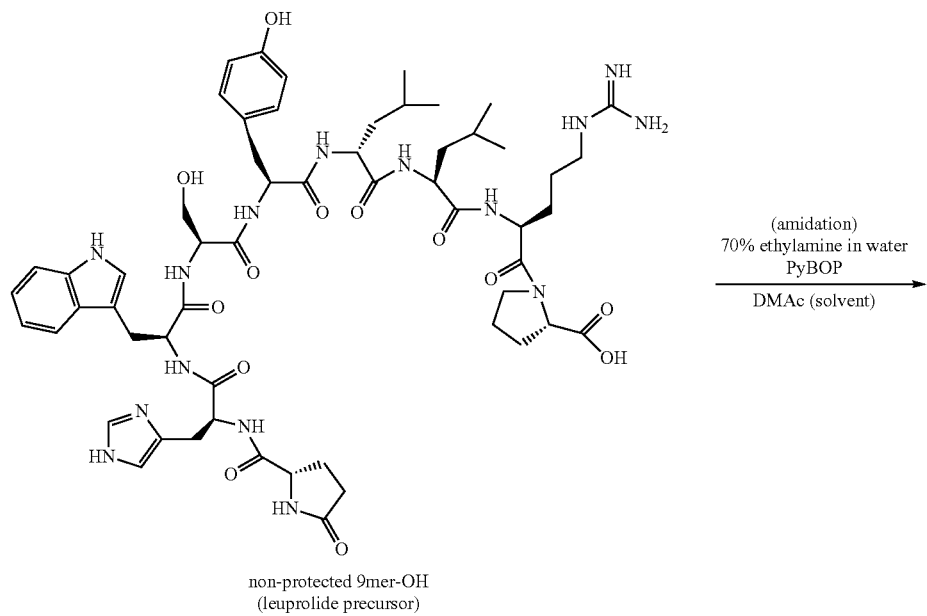
non-protected 9mer-OH
(leuprolide precursor)
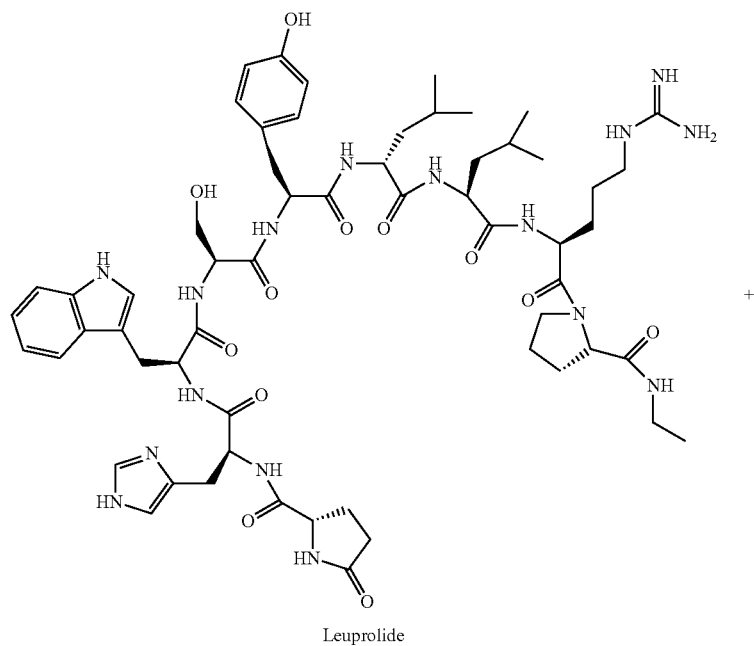
Leuprolide -continued

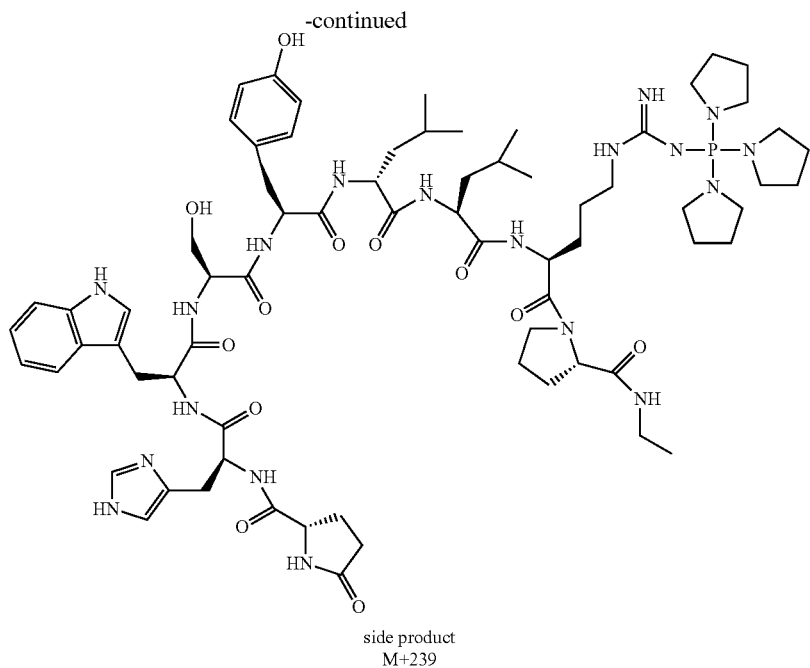

side product
M+239

The inventive process utilizes an excess equivalent of ethyl amine to react with the deprotected leuprolide precursor in the presence of a suitable coupling reagent to obtain leuprolide. Surprisingly, it is noted that although the use of an excess equivalent of ethyl amine can induce a major side product of "M+239" shown in Scheme 1, controlling the excess equivalent not more than 7 equivalents can control "M+239" to less than 1% and thus providing a high yield and high purity of leuprolide. See the Table A as shown below.

TABLES A

| Amidation condition and "M + 239" content | | |
|---|---|---|
| PyBOP | Ethylamine | % of "M + 239" by HPLC |
| 1.8 eq | 5 eq | <1% |
| 2.3 eq | 5 eq | <1% |
| 1.5 eq | 6 eq | <1% |
| 1.8 eq | 7 eq | <1% |
| 1.4 eq | 10 eq | 4% |
| 1.9 eq | 10 eq | 5% |

In some embodiments, the inventive process reacts the deprotected leuprolide precursor with a specific equivalent of 70 wt % ethyl amine aqueous solution in the presence of a suitable coupling reagent to obtain leuprolide, wherein the specific equivalent of about 70 wt % ethyl amine is preferably not more than about 10 equivalents, more preferably not more than about 7 equivalents in comparison with the equivalent of the deprotected leuprolide precursor.

In some embodiments, the inventive process utilizes a suitable coupling reagent to treat the coupling reaction between the deprotected leuprolide precursor and ethyl amine, wherein the suitable coupling reagent is PyBOP, and preferably the amount of the suitable coupling reagent is in a range of 1~2 equivalents in comparison with the equivalent of the deprotected leuprolide precursor. One of skill in the art will appreciate that still other coupling reagents may be useful in the inventive process.

The inventive process comprises providing a protected amino acid, attached in its C-terminal to an acid-labile resin; coupling said protected amino acid with another protected amino acids step by step in the presence of an coupling reagent to obtain a amino acid derivative attached in its C-terminal to an acid-labile resin.

In some embodiments, the coupling reagent utilized for step by step preparing the protected amino acid derivative attached in its C-terminal to an acid-labile resin is selected from O-Benzotriazole-N,N,N',N'-tetramethyl-uronium-hexafluoro-phosphate (HBTU)/N-hydroxybenzotriazole hydrate (HOBT hydrate), or 3-(diethoxy-phosphoryloxy)-3H-benzo[d][1,2,3]triazin-4-one (DEPBT).

Optionally, the coupling reactions of preparing the protected amino acid derivative attached in its C-terminal to an acid-labile resin comprises adding a base. Preferably, the base is selected from diisopropylethylamine (DIPEA).

EXAMPLES

The following examples are presented to illustrate, but not limit, certain aspects of the present invention.

Abbreviations utilized in the Examples include:

Fmoc, fluorenylmethyloxycarbonyl; SPPS, solid phase peptide synthesis; 2-CTC, 2-Chlorotrityl chloride; HMPA-NovaGel™, 4-Hydroxymethylphenoxyacetyl NovaGel™ resin; DCM, Dichloromethane; DIPEA, Diisopropylethylamine; DMAc, N,N'-Dimethylacetamide; Pyr, Pyroglutamic acid; His, Histidine; Trp, Tryptophane; Ser, Serine; Tyr, Tyrosine; D-Leu, D-optically active leucine; Leu, Leucine; Arg, Arginine; Pro, Proline; HOBt, 1-Hydroxybenzotriazole; DIC, N,N'-Diisopropylcarbodiimide; MTBE, Methyl tert-butyl ether; TFA, Trifluoroacetic acid; TIS, Triisopropylsilane; EDT, Ethanedithiol; HBTU, O-Benzotriazole-N,N,N',N'-tetramethyl-uronium-hexafluoro-phosphate; DEPBT, 3-(Diethoxy-phosphoryloxy)-3H-benzo[d][1,2,3]triazin-4-one; DIC, N,N'-Diisopropylcarbodiimide; EDCI, 1-Ethyl-3-(3-dimethylaminopropyl)carbodiimide; PyBOP, Benzotriazol-1-yl-oxytripyrrolidinophosphonium hexafluorophosphate; ACN, Acetonitrile

Example 1

Preparation of Pyr-His-Trp-Ser-Tyr-D-Leu-Leu-Arg-Pro-OH by 2-CTC Resin (Deprotected Leuprolide Precursor)

Synthesis of the non-protected peptide was carried out by a stepwise Fmoc-SPPS (solid phase peptide synthesis) strategy starting from the loading of Fmoc-Pro-OH to 2-CTC resin. The resin was swelled in DCM (500 mL, 10 parts based on blank resin) for 30 min and stirred with a solution of Fmoc-Pro-OH (43.9 g, 2 eq.) in DCM 300 mL in the presence of DIPEA (34.0 mL, 3 eq.) for 2 hr, and the resin was slurry washed in DCM (300 mL, 6 parts) for three times and in DMAc (300 mL, 6 parts) for one time.

The Fmoc protecting group was then removed by treatment of 20% piperidine in DMAc (v/v) (300 mL, 6 parts) twice, and the residual piperidine was removed by slurry washing of the resin in DMAc (300 mL, 6 parts) for six times. The 6th filtrate was checked by the Chloranil test to provide the N-terminal released resin. The Fmoc-protected amino acid Note (1.5 eq.) was coupled with the N-terminal released resin after activation in situ with coupling reagents[Note] and DIPEA (26.0 mL, 2.3 eq.) in DMAc (300 mL, 6 parts) for 2 hours, and the completion of the reaction was monitored by the Kaiser test. The resin was slurry washed in DMAc (300 mL, 6 parts) for four times. According to the peptide sequence, the coupling steps described above were repeated with other amino acids to afford the target peptide except the last amino acid, Pyr.

In order to introduce Pyr to the N-terminal released resin, the DMAc solution (300 mL, 6 parts) of Pyr (12.6 g, 1.5 eq.) and HOBt hydrate (14.9 g, 1.5 eq.) were added into N-terminal released resin, and DIC (30.5 mL, 3 eq.) was employed as the coupling reagent. The mixture was stirred for 2 hours and the completion of the reaction was monitored by the Kaiser test. The resin was then slurry washed in DMAc (300 mL, 6 parts) for four times and in MTBE (300 mL, 6 parts) for three times. The wet resin (9-mer) was vacuum dried at 25° C. under nitrogen to give 9mer-resin as a yellow to light yellow solid (133 g).

The 9-mer-resin (76.6 g) described above was deblocked by TFA (432 mL, 90% v/v), TIS (29 mL, 6% v/v), EDT (9.6 mL, 2% v/v) and H2O (9.6 mL, 2% v/v) as deblocking reagent for 2 hours, and the deblocking reaction solution was collected by filtration, and the resin was rinsed by TFA (320 mL). Combined filtrates and cooled to 0 to 10° C. MTBE (1600 mL) was added to precipitated solid, filtered, and washed by MTBE (320 mL) two times. The wet cake was suction dried under N2 gas overnight to give non-protected 9-mer-OH (deprotected leuprolide precursor, as Pyr-His-Trp-Ser-Tyr-D-Leu-Leu-Arg-Pro-OH) (29.6 g).

Note: The coupling reagents utilized with Fmoc-Arg(Pbf)-OH (63.3 g), Fmoc-Leu-OH (34.5 g), Fmoc-D-Leu-OH (34.5 g), Fmoc-Tyr(tBu)-OH (44.8 g) and Fmoc-Trp(Boc)-OH (51.3 g) were HBTU (37.0 g, 1.5 eq.) and HOBt hydrate (14.9 g, 1.5 eq.); The coupling reagent utilized with Fmoc-Ser(tBu)-OH (37.4 g) and Fmoc-His(Trt)-OH (60.4 g) was DEPBT (29.2 g, 1.5 eq.).

Example 2

Preparation of Pyr-His-Trp-Ser-Tyr-D-Leu-Leu-Arg-Pro-NHEt (Leuprolide)

9mer-OH (28.2 g) was mixed with ethylamine (70% aqueous solution, 11.5 mL, 6 eq) in DMAc (141 mL, 5 parts). PyBOP (14.9 g, 1.2 eq.) was added and reacted for 30 min. PyBOP (3.7 g, 0.3 eq) was added and the reaction was monitored by HPLC. The crude product was precipitated by ACN (1127 mL, 40 parts) at 0 to 10° C., filtered, and washed by ACN (150 mL×2) and MTBE (150 mL) in turn. The wet cake was suction dried under N2 to give crude lueprolide (26.3 g, MS calculated for $C_{59}H_{84}N_{16}O_{12}$ 1208.65, found M+H 1209.65).

Example 3

Preparation of Pyr-His-Trp-Ser-Tyr-D-Leu-Leu-Arg-Pro-OH by HMPA-NovaGel™ (Deprotected Leuprolide Precursor)

Synthesis of the non-protected peptide was carried out by a stepwise Fmoc SPPS (solid phase peptide synthesis) strategy starting from the loading of FmocProOH to HMPA-NovaGel™ resin. The resin (HMPA-NovaGel™ resin, 1.0 g) was swelled in DCM (10 mL, 10 parts based on blank resin) for 30 min and stirred with a solution of FmocProOH (0.53 g, 3 eq.) in DCM 10 mL in the presence of DMAP (12.7 mg, 0.2 eq.) and DIC (0.41 mL, 5 eq.) for 2 hr, and then further added DIC (0.41 mL, 5 eq.) to the resulting slurry for 1 h. The resin was slurry washed in DMAc (10 mL, 10 parts) for three times.

The Fmoc protecting group was then removed by treatment of 20% piperidine in DMAc (v/v) (10 mL, 10 parts) twice, and the residual piperidine was removed by slurry washing of the resin in DMAc (10 mL, 10 parts) for six times. The 6th filtrate was checked by the Chloranil test to provide the N-terminal released resin. The Fmoc-protected amino acid[Note] (3-4 eq.) was coupled with the N-terminal released resin after activation in situ with coupling reagents Note and DIPEA (0.41 mL, 4.5 eq) in DMAc (10 mL, 10 parts) for 2 hr, and the completion of the reaction was monitored by the Kaiser test. The resin was slurry washed in DMAc (10 mL, 10 parts) for four times. According to the peptide sequence, the coupling steps described above were repeated with other amino acids to afford the target peptide except the last amino acid, Pyr.

Note: The coupling reagents used with FmocLeu-Arg(Pbf)OH (1.585 g, 4 eq.), Fmoc-D-LeuOH (0.551 g, 3 eq.), Fmoc-Tyr(tBu)OH (0.717 g, 3 eq.), and FmocTrp(Boc)OH (0.821 g, 3 eq.) were HBTU (0.582 g, 2.95 eq.) and HOBt hydrate (0.239 g, 3 eq.); The coupling reagent used with FmocSer(tBu)OH (0.598 g, 3 eq.) and FmocHis(Trt)OH (0.967 g, 3 eq.) was DEPBT (0.459 g, 2.95 eq.)

In order to introduce Pyr to the N-terminal released resin, the DMAc solution (10 mL, 10 parts) of Pyr (0.201 g, 3 eq) and HOBt hydrate (0.239 g, 3 eq) were added into N-terminal released resin, and DIC (0.611 mL, 7.5 eq.) was employed as the coupling reagent. The mixture was stirred for 2 hr and the completion of the reaction was monitored by the Kaiser test. The resin was then slurry washed in DMAc (10 mL, 10 parts) for four times and in MTBE (10 mL, 10 parts) for three times. The wet resin (9mer) was vacuum dried at 25° C. under nitrogen to give 9mer-resin as a yellow to light yellow solid (1.80 g).

The 9mer-resin (1.80 g) described above was deblocked by TFA (16.2 mL, 90% v/v), TIS (1.1 mL, 6% v/v), EDT (0.4 mL, 2% v/v) and H2O (0.4 mL, 2% v/v) as deblocking reagent for 2 hr, and the deblocking reaction solution was collected by filtration, and the resin was rinsed by TFA (40 mL). Combined filtrates and concentrated to about 25 mL, then cooled to 0~10 C.°. MTBE (50 mL) was added to precipitated solid, filtered, and washed by MTBE (20 mL) three times. The wet cake was suction dried under N2 overnight to give non-protected 9mer-OH (deprotected leuprolide precursor, as Pyr-His-Trp-Ser-Tyr-D-Leu-Leu-Arg-Pro-OH) (0.47 g).

Example 4

Preparation of Pyr-His-Trp-Ser-Tyr-D-Leu-Leu-Arg-Pro-NHEt (Leuprolide)

9mer-OH (0.4 g) from Example 3 was mixed with ethylamine (70% aqueous solution, 0.16 mL, 6 eq) in DMAc/ACN=3/2 (2 mL, 5 parts). PyBOP (0.21 g, 1.2 eq.) was added and reacted for 30 min. PyBOP (0.05 g, 0.3 eq) was added and the reaction was monitored by HPLC. The crude product was precipitated by ACN (16 mL, 40 parts) at 0~10° C., filtered, and washed by ACN (5 mL×2) and MTBE (5 mL×3) in turn. The wet cake was suction dried under N2 to give crude lueprolide (0.32 g, MS calcd for $C_{59}H_{84}N_{16}O_{12}$ 1208.65, found M+H 1209.7).

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

We claim:

1. A process for the preparation of leuprolide or a pharmaceutically acceptable salt thereof comprising:
   providing a protected leuprolide precursor attached in its C-terminal to an acid-labile resin, wherein the protected leuprolide precursor comprises multiple amino acids in the following sequence: Pyr-His (P1)-Trp (P2)-Ser (P3)-Tyr (P4)-D-Leu-Leu-Arg (P5)-Pro-OH, each of P1, P2, P3, P4, and P5 independently represents a protecting group for the side chain of the corresponding amino acid;
   cleaving P1, P2, P3, P4, and P5 of said protected leuprolide precursor and said resin in one step by reacting said protected leuprolide precursor attached in its C-terminal to the acid-labile resin with an acidic solution to obtain a deprotected leuprolide precursor with the following amino acid sequence of: Pyr-His-Trp-Ser-Tyr-D-Leu-Leu-Arg-Pro-OH;
   amidating the deprotected leuprolide precursor with ethylamine in the presence of a coupling reagent to provide leuprolide, wherein the amount of ethylamine used in the amidating step is larger than one but no greater than seven molar equvants of the deprotected leuprolide precursor; and
   obtaining the leuprolide or converting the leuprolide into a pharmaceutically acceptable salt thereof.

2. The process of claim 1 wherein the step providing comprises synthesis cycles whereby in each such synthesis cycle a designated amino acid is added to a growing peptide chain attached to the acid-labile resin in the presence of a coupling reagent and a base by formation of a peptide linkage between an amino group of the growing peptide chain and a carboxyl group of the designated amino acid to produce said protected leuprolide precursor attached in its C-terminal to the acid-labile resin.

3. The process of claim 2, wherein the coupling reagent for the synthesis cycles is selected from the group consisting of O-benzotriazole-N,N,N',N'-tetramethyl-uronium-hexafluoro-phosphate (HBTU)/N-hydroxybenzotriazole hydrate (HOBT hydrate) and 3-(diethoxy-phosphoryloxy)-3H-benzo[d][1,2,3]triazin-4-one (DEPBT).

4. The process of claim 2, wherein said base is diisopropylethylamine (DIPEA).

5. The process of claim 1, wherein the suitable acidic solution is a solution comprising at least 80 volume % of trifluoroacetic acid (TFA).

6. The process of claim 1, wherein said acid-labile resin is selected from the group consisting of: 2-chlorotrityl chloride (2-CTC) resin and 4-hydroxymethylbenzoic acid aminomethyl (HMPA) resin.

7. The process of claim 6, wherein said acid-labile resin is 2-chlorotrityl chloride (2-CTC) resin.

8. The process of claim 1 comprising obtaining the deprotected leuprolide precursor by isolation prior to the amidating step.

9. The process of claim 8, wherein the isolation is carried out by precipitation, crystallization, extraction or chromatography.

10. The process of claim 9, wherein the isolation is carried out by precipitation.

11. The process of claim 1, wherein the coupling reagent for the amidating step is selected from the group consisting of N,N'-diisopropylcarbodiimide (DIC), 1-ethyl-3-(3-dimethylaminopropyl)carbodiimide (EDCI), and benzotriazol-1-yl-oxytripyrrolidinophosphonium hexafluorophosphate (PyBOP).

12. A process for preparing a leuprolide acid addition salt comprising:
   obtaining leuprolide according to claim 1, and
   converting the obtained leuprolide into the salt.

* * * * *